United States Patent [19]
Ninomiya et al.

[11] Patent Number: 5,945,448
[45] Date of Patent: Aug. 31, 1999

[54] BRAIN EDEMA INHIBITOR

[75] Inventors: Mitsuyoshi Ninomiya, Kobe; Yoshiyuki Matsuo, Osaka, both of Japan

[73] Assignee: Shionogi & Co., Ltd., Japan

[21] Appl. No.: 08/930,827

[22] PCT Filed: May 29, 1996

[86] PCT No.: PCT/JP96/01438

§ 371 Date: Oct. 10, 1997

§ 102(e) Date: Oct. 10, 1997

[87] PCT Pub. No.: WO96/38173

PCT Pub. Date: Dec. 5, 1996

[30] Foreign Application Priority Data

Jun. 2, 1995 [JP] Japan .................................. 7-160060

[51] Int. Cl.$^6$ .......................... A01N 37/00; A61K 31/21; C07C 229/00; C07C 69/76
[52] U.S. Cl. ........................ 514/510; 514/870; 560/43; 560/75
[58] Field of Search .................... 514/510, 870; 560/75, 43

[56] References Cited

U.S. PATENT DOCUMENTS

| | | | |
|---|---|---|---|
| 5,248,807 | 9/1993 | Fujimoto et al. | 560/75 |
| 5,463,107 | 10/1995 | Konoike et al. | 560/43 |
| 5,599,811 | 2/1997 | Berryman et al. | 514/226.5 |

OTHER PUBLICATIONS

Stanimirovic et al., "Arachidonic acid release and permeability changes induced by endothelins in human cerebromicrovascular endothelium", Acta Neurochir, 60, 71–75, 1994.

Mihara et al., "Pharmacological characterization of a potent nonpeptide endothelin receptor antagonist, 97–139", The Journal of Pharmacology and Experimental Therapeutics, 268 (3), 1122–27, 1994.

D.B. Stanimirovic et al., *Acta Neurochir*, 60, 71–75 (1994) [Suppl.].

F.C. Barone et al., *J. Card. Pharm.*, 26(Suppl.3), S404–S407 (1995).

J.Y. Lee et al., *Pharmacology*, 49, 319–324 (1994).

K. Kasumoto et al., *Life Sciences*, 55(4), 301–310 (1994).

M. Ihara et al., *Life Sciences*, 50(4), 247–255 (1992).

J. Filep et al., *Br. J. Pharmacol.*, 113, 834–852 (1994).

J. Lee et al., *Biochemistry*, 33, 14543–14549 (1994),

D.L. Williams et al., *Journal of Pharmacology and Experimental Therapeutics*, 275(3), 1518–1526 (1995).

J. Filep et al., *Br. J. Pharmacol.*, 112, 963–971 (1994).

*Primary Examiner*—S. Mark Clardy
*Assistant Examiner*—Marina Lamm
*Attorney, Agent, or Firm*—Wenderoth, Lind & Ponack

[57] ABSTRACT

The present invention relates to a composition for treating or preventing brain edemas which comprises containing an endothelin antagonist as an active ingredient, for example, the compound of the following formula (I):

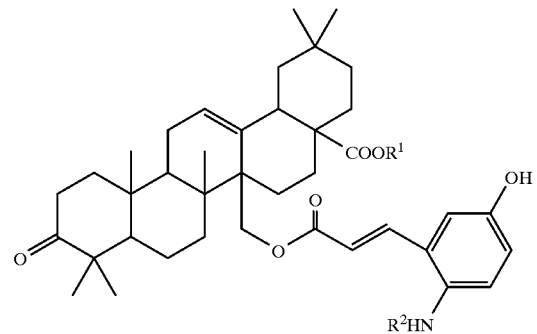

(I)

or pharmaceutically acceptable salts or hydrates thereof, bosentan, cyclo[D-aspartyl-L-[3-(4-phenylpiperazin-1-ylcarbonyl)]-alanyl-L-aspartyl-D-[2-(2-thienyl)]glycyl-L-leucyl-D-tryptophyl]disodium or cyclo [D-Asp-L-Pro-D-Val-L-Leu-D-Trp].

Furthermore, the present invention provides a method for treating or preventing brain edemas, which comprises administering an effective amount of an endothelin antagonist and use of an endothelin antagonist for the manufacture of a medicament for treating or preventing brain edemas.

An endothelin antagonist exhibits an inhibitory effect, on all brain edemas regardless of the onset mechanism and thus is highly useful in the treatment or prevention of brain edemas.

1 Claim, 3 Drawing Sheets

BRAIN EDEMA INHIBITOR

FIELDS OF THE INVENTION

The present invention relates to a composition for treating or preventing brain edemas which comprises containing an endothelin antagonist as an active ingredient.

BACKGROUND OF THE INVENTION

Brain edemas means such a state of the brain that water in a living body has unusually accumulated inside of the brain parenchyma to increase the volume of the brain tissue. As for the factors inducing brain edemas, for example, cerebrovascular diseases such as stroke, head injury, brain tumor, hypertension, respiratory insufficiency, CO poisoning, hyponatremia, acute nephropathy, disequilibrium syndrome caused by hemodialysis, hyperglycemia, hypoglycemia, adrenal insufficiency, collagen diseases, and tin, lead or arsenical poisoning are exemplified. Particularly, a treatment of brain edemas which are caused in an acute phase of stroke or by head injury is a very important problem to be solved. Furthermore, brain edemas are likely to cause a cerebral cerebral hernia, a headache, nausea, vomiting, restless, convulsions, clouding of consciousness and the like. Particularly, a deterioration of a cerebral hernia sometimes causes the patients to die.

Brain edemas are classified into cytotoxic edemas, vasogenic edemas and the like according to the mechanisms of the occurrence, but these types of edemas often appear together, and so the etiology of brain edemas has not been clear enough. It is desired to make the etiology clear and establish the method for the treatment.

Currently, hyperosmotic medicaments or adrenocortical steroids and the like have been used for treating brain edemas.

As hyperosmotic medicaments, 10% glycerol, 5% fructose-added physiological saline, 15% or 20% mannitol and the like may be exemplified. Intravenous administration of these hypertonic medicaments raises blood osmotic pressure to produce a difference of the pressure between the brain parenchyma tissues and the blood; as a result water accumulated in the brain tissues moves into the bloodstream to improve brain edemas. Furthermore, these medicaments are characterized by slight side effects since they scarcely pass through the blood brain barrier to reach the brain parenchyma tissues. But even for these medicaments, the accumulation in a brain in some degree cannot entirely be avoided, when the blood concentration reach high by a large quantity administration. In case a blood brain barrier is injured, the medicaments easily move to the brain; if the blood concentration of the medicaments decreases after stopping to administer the medicaments and the osmotic pressure in the brain tissue becomes higher than that in the blood, water in the blood could move back to the brain parenchyma tissue and brain edemas might appear again. These medicaments also have side effects such as electrolytic aberration, nephropathy and the like.

As for adrenocortical steroids, dexamethasone, hydrocortisone and the like are exemplified. These adrenocortical steroids exhibit ameliorative effects on brain edemas around brain tumors, but these have little effects on ischemic and traumatic brain edemas and exhibit side effects such as digestive tract hemorrhage, infectious disease exacerbation, diabetes exacerbation and the like.

Recently, calcium antagonists such as Nimodipine, Nicardipine, NC-1100 and the like have attracted attention as alternative medicaments for treating brain edemas. It is reported that the pretreatment with these calcium antagonists delays the progress of cellular brain edemas. MK-801, a glutamate antagonist, is also known to exhibit an inhibitory effect on brain edemas. These calcium antagonists and glutamate antagonists which have inhibitory effects on brain edemas, however, have not yet been used clinically.

DISCLOSURE OF THE INVENTION

In the above situations, the present inventors have studied intensively to develop medicaments which have superior inhibitory effects on brain edemas, and found that endothelin antagonists inhibit brain edemas.

Thus, the present invention provides a composition for treating or preventing brain edemas which comprises containing an endothelin antagonist as an active ingredient. The present invention provides a method for treating or preventing brain edemas, which comprises administering an effective amount of an endothelin antagonist. The present invention relates to use of an endothelin antagonist for the manufacture of a medicament for treating or preventing brain edemas.

Currently, an endothelin antagonist has been reported only to have the possibility to be a medicament for treating or preventing diseases caused by endothelin, for example, cerebral vasoconstriction after subarachnoid hemorrhage, hypertension, ischemic disorders, cerebral circular disorders, renal insufficiency, asthma and the like.

In the present specification, the term "endothelin antagonist" includes all compounds which have endothelin antagonist activity, and any compounds which have endothelin antagonist activity can preferably be used for the present invention. The typical examples of such compounds example include compounds of the following formula (I):

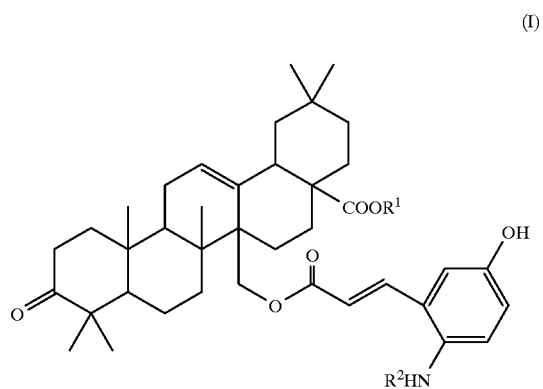

(I)

wherein $R^1$ is hydrogen or a metabolizable ester residue; $R^2$ is hydrogen or $-R^3-R^4$ wherein $R^3$ is $-SO_3-$, $-CH_2COO-$, $-COCOO-$, or $-COR^5COO-$, wherein $R^5$ is alkylene having 1 to 6 carbon atoms or alkenylene having 2 to 6 carbon atoms, and $R^4$ is hydrogen or alkyl having 1 to 6 carbon atoms (hereinafter referred to as Compound (I)), pharmaceutically acceptable salts (WO92/12991, JP-A 7-53484) or hydrates thereof, bosentan (p-tert-butyl-N-[6-(2-hydroxyethoxy)-5-(o-methoxyphenoxy)-2-(2-pyrimidinyl)-4-pyrimidinyl]-benzenesulfonamide; British Journal of Pharmacology, 1994. November, 113(3) 845–852), cyclo[D-aspartyl-L-[3-(4-phenylpiperazin-1-ylcarbonyl)]-alanyl-L-aspartyl-D-[2-(2-thienyl)]glycyl-L-leucyl-D-tryptophyl]disodium (hereinafter referred to as TAK-044; Life Science 1994, 55(4), 301–310), cyclo[D-

Asp-L-Pro-D-Val-L-Leu-D-Trp] (hereinafter referred to as BQ-123; Life Science, 1992, 50, 247–255), 2(R)-[2(R)-[2 (S) [[1-(hexahydro-1H-azepinyl)]carbonyl]amino-4-methylpentanoyl]amino-3-[3-(1-methyl-1H-indolyl)] propionyl]amino-3-(2-pyridyl)propionic acid (FR139317; Pharmacology 1994, 49(5), 319–324), (1S,2R,3S)-3-(2-carboxymethoxy-4-methoxyphenyl)-1-(3,4-methylenedioxyphenyl)-5-prop-1-yloxy)indan-2-carboxylic acid (SB-209670; Biochemistry, 1994, December, 33(48), 14543–14549), 3-benzo-[1,3]-dioxol-5-yl-5-hydroxy-5-(4-methoxyphenyl)-4-(2,3,4-trimethoxybenzyl)-5H-furan-2-one (PD-156123; International Publication No. WO95/05376), and (−)-N-(4-isopropylbenzenesulfonyl)-α-(4-carboxy-2-n-propylphenoxy)-3,4-methylenedioxyphenylacetamide(L-754142; The Journal of Pharmacology and Experimental Therapeutics 1995, 275(3), 1518–1526) and the like.

THE PREFERRED EMBODIMENTS OF THE INVENTION

Figure 1:
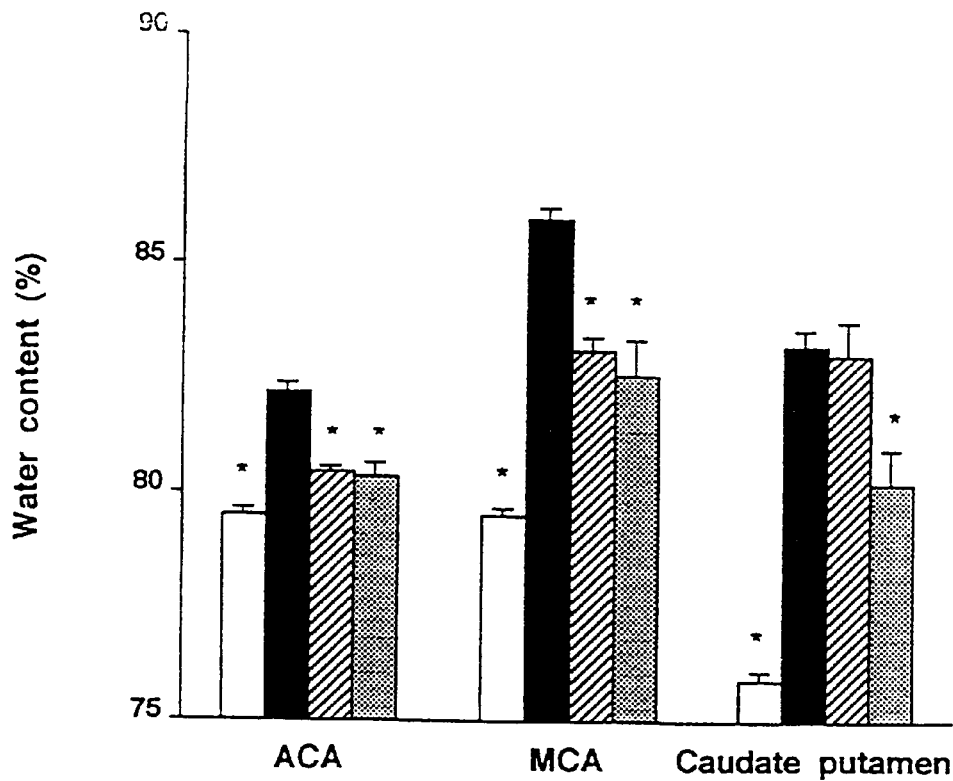
FIG. 1 shows an effect of Compound (I—Na) on brain edemas. The ordinate represents the brain water content (%) and the abscissa represents the parts of brain. "ACA", "MCA" and "Caudate putamen" means a cerebral cortex supplied by an anterior cerebral artery and a cerebral cortex supplied by middle cerebral artery and a striatum, respectively. The bars from the left, respectively represent a sham-operation group (N=5), a vehicle-administered group (N=13), a pre-ischemic administered group (N=6), and a post-ischemic administered group (N=7). Data are represented by means with a standard error. The significant difference with P value <0.05 from a vehicle-administered group is represented by the asterisk.

In the present invention, any compounds which have endothelin antagonist activity can preferably be used as an endothelin antagonist. Specifically, exemplified are Compound (I), pharmaceutically acceptable salts and hydrates thereof, bosentan, TAK-044, and BQ-123 and the like. Compound (I) and pharmaceutically acceptable salts and hydrates thereof are preferable and compound (I) wherein $R^1$ is hydrogen and $R^2$ is —COCH═CHCOOH, and pharmaceutically acceptable salts and hydrates thereof are particularly preferable.

In the present specification, "metabolizable ester residue" means an ester residue which is hydrolyzed in a living body to produce a biologically active carboxylic acid group.

Examples of the above metabolizable ester residue include alkyl having 1 to 6 carbon atoms such as methyl, ethyl, tert-butyl and the like; aryl such as phenyl and the like; (1-acyloxy)alkyl such as pivaloyloxymethyl, acetoxymethyl, 1-acetoxyethyl and the like; 1-(alkyloxycarbonyloxy)alkyl such as 1-(ethoxycarbonyloxy)ethyl, 1-(isopropoxycarbonyloxy)ethyl and the like; and (5-methyl-1,3-dioxolen-4-yl)methyl and the like.

The term "alkyl having 1 to 6 carbon atoms" means straight or branched alkyl, and methyl, ethyl, propyl, tert-butyl and the like are exemplified. The term "alkyl" means the same as above.

As for the "alkylene having 2 to 6 carbon atoms", for example, methylene, ethylene, trimethylene and the like are exemplified. Preferable embodiments are groups shown by the formula —(CH═CH)m— (m represents an integer of 1–3).

The compound (I) may form its pharmaceutically acceptable salts, for example, with mineral acids such as hydrochloric acid, sulfuric acid, nitric acid, phosphoric acid, hydrofluoric acid, hydrobromic acid etc.; with organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid etc.; with organic bases such as ammonium, trimethyl ammonium, triethyl ammonium etc.; with alkali metals such as sodium, potassium etc., or with alkaline earth metals such as calcium, magnesium and the like.

The compound (I) may form its hydrates and may coordinate to one or more molecules of water per molecule of the compound (I).

The composition for treating or preventing brain edemas of the present invention has an effect of decreasing intracranical pressure and exhibits an inhibitory effect on all types of brain edemas regardless of the onset mechanism, and it is highly useful for treating ischemic and traumatic brain edemas. Moreover, it has an ameliorative effect on infarction.

The composition for brain edemas of the present invention is effective for treating or preventing brain edemas when it is administered in the situation that brain edemas have been caused or may be caused in, for example, cerebrovascular disease such as stroke, head injury, brain tumor and the like. Moreover, the composition for brain edemas of the present invention is also effective for treating or preventing cerebral hernia, clouding of consciousness, and the like caused by brain edemas. It is also effective for the treatment of brain edemas caused in acute phase of stroke and by head injury.

When the composition for brain edemas of the present invention is applied as a pharmaceutical composition, it can safely be administered either orally or parenterally. In case of an oral administration, it may be in any usual forms such as tablets, granules, powders, capsules, pills, solutions, suspensions, syrups, buccal tablets, sublingual tablets and the like for the administration. When the composition is parenterally administered, any usual forms are preferable, for example, injections such as intravenous injections or intramuscular injections, suppositories, endermic agents, inhalations and the like and the intravenous injection is particularly preferable.

A pharmaceutical composition of the present invention may be manufactured by if necessary mixing an effective amount of an active ingredient with various pharmaceutical ingredients suitable for the final administration form, such as excipients, binders, moistening agents, disintegrators, lubricants, and diluents. When the composition is of an injection, an active ingredient can be sterilized with a suitable carrier to give a pharmaceutical composition.

Specifically, examples of the excipients include lactose, saccharose, glucose, starch, calcium carbonate, crystalline cellulose and the like, examples of the binders include methylcellulose, carboxymethylcellulose, hydroxypropylcellulose, gelatin, polyvinylpyrrolidone and the like, examples of the disintegrators include carboxymethylcellulose, sodium carboxymethylcellulose, starch, sodium alginate, agar, sodium lauryl sulfate and the like, and examples of the lubricants include talc, magnesium stearate, macrogol and the like. Cacao oil, macrogol, methyl cellulose and the like may be used as base materials of suppositories. When the composition is manufactured as solutions, emulsified injections or suspended injections, dissolving accelerators, suspending agents, emulsifiers, stabilizers, preservatives, isotonic agents and the like may be added, and when it is manufactured for an oral administration, sweetening agents, flavors and the like may be added.

Although a dosage of the compound as a brain edema inhibitor should be established in consideration of the patient's age, body weight, administration route, type and degree of diseases, the compound may usually be administered orally in a single or divided doses of 1 µg–200 mg/kg/day for an adult. In case that it is parenterally administered, although the dosage highly depends on an administration route, the compound may be administered in a single or divided doses of 0.1 µg–20 mg/kg/day.

EXAMPLE

The present invention is further explained by the following Examples and Experiments, which are not intended to limit the scope of the present invention.

Experimental Method (1) Animals for experiment

Male Wistar rats of 12 weeks old (270 g to 320 g, Japan SLC, Inc.) were subjected to pre-feeding for at least a week, and used for the experiment.

(2) Preparation of focal cerebral ischemia-reperfusion model

We prepared focal cerebral ischemia-reperfusion models by modifying the method of Longa et al. (Stroke, 1989, vol.20 pp.84–91) Rats were anesthetized with 2% halothane and the right common carotid artery was exposed and the right external carotid artery (ECA) was carefully ablated, ligated and cut. The right external carotid artery was turned over and a 4-0 nylon thread coated with silicon (18 mm) was inserted from the right external carotid artery to the right internal carotid artery to occlude the origin of the right middle cerebral artery. The end of the thread was ligated to the external carotid artery to prevent the blood flowing backward and the anesthesia was discontinued. After the discontinuation of the anesthesia, the rat body temperature were maintained at 37° C. and the rats showing the hemiparesis in the left-sided fore-leg within 15 minutes were used in the following experiments as ischemia load models. After 60 minutes of the middle cerebral artery occlusion, the rats were anesthetized again and the threads were removed to allow reperfusion of the ischemic area via the right common carotid artery.

(3) Method of measurement of brain edemas (brain water content)

After 24 hours of the ischemia-reperfusion, the rats were decapitated under the anesthesia with pentbarbital and the brains were taken out. The brains were separated with tweezers in a humidifier into 3 parts: (a) cerebral cortex supplied by anterior cerebral artery (ischemia-contiguous cortex; ACA), (b) cerebral cortex supplied by middle cerebral artery (ischemic cortex; MCA) and (c) caudate putamen (ischemic core). After the wet weight of each sample was measured, the samples were dried at 105° C. for 24 hours to measure the dry weight. The water content was calculated according to the following formula and used as an index of the brain edema.

Brain water content (%)=(wet weight−dry weight)/wet weight×100

Experiment 1

Inhibitory effect of compound (I—Na) on brain edemas in pre-ischemic administration and post-ischemic administration A compound represented by the formula (I) in which $R^1$ is Na and $R^2$ is —COCH═CHCOONa (hereinafter referred to as compound (I—Na)) was dissolved in physiological saline and used as an endothelin antagonist.

In the pre-ischemic administration group, an osmotic pressure pump filled with the compound (I—Na) was subcutaneously buried in the back of a rat 24 hours before the middle cerebral artery occlusion (ischemic burden) and the compound (I—Na) was administered by a continuous hypodermic administration (12 mg/kg/day) from 24 hours before the ischemic load to 24 hours after the reperfusion. In the post-ischemic administration group, the compound (I—Na) was administered by an intravenous injection (12 mg/kg) immediately after the reperfusion from the tail vein (bolus administration) and further administered by a continuous hypodermic administration (12 mg/kg/day) from 10 minutes to 24 hours after the reperfusion.

Twenty four hours after the reperfusion, the brain water content in the ischemic area increased significantly in the vehicle-administered group compared with that of the sham operation group. This means the formation of the brain edemas in the former group.

The pre-ischemic administration of the compound (I—Na) suppressed the formation of brain edemas significantly in the ACA and MCA areas but not in the caudate putamen (FIG. 1).

The post-ischemic administration of the compound (I—Na) significantly suppressed the formation of the brain edemas not only in the ACA and the MCA areas but also in the caudate putamen (FIG. 1). This result means that even in the post-ischemic administration of the compound (I—Na) the formation of the brain edemas remarkably is suppressed.

Experiment 2

Figure 2:
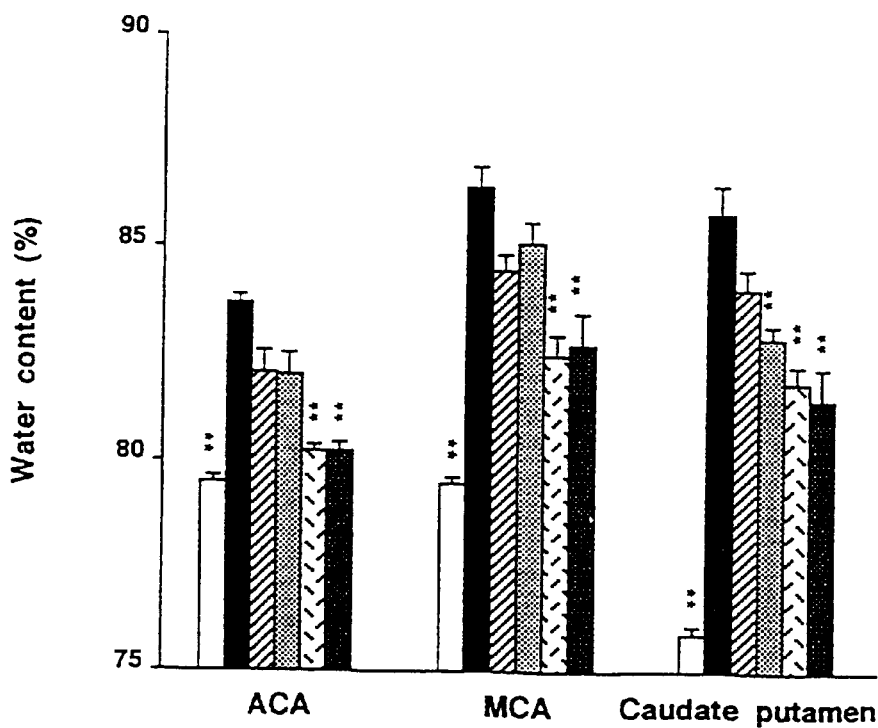
FIG. 2 shows dose-dependent effects of Compound (I—Na) on brain edemas. The ordinate represents the brain water content (%) and the abscissa represents the parts of brain. "ACA", "MCA" and "Caudate putamen" represents the same as described above. The bars from the left, respectively represent a sham-operation group (N=5), a vehicle-administered group (N=13), a group (N=6) to which Compound (I—Na) administered at a 0.03 mg/kg/hr dose, a group (N=7) to which Compound (I—Na) administered at a 0.1 mg/kg/hr dose, a group (N=6) to which Compound (I—Na) administered at a 0.3 mg/kg/hr dose, and a group (N=6) to which Compound (I—Na) administered at a 1.0 mg/kg/hr dose. Data are represented by means with a standard error. The significant differences with P values <0.05 and <0.01 from a vehicle administered group are represented by the asterisk and double asterisks.

The influence of the dose of the compound (I—Na) on the inhibitory effect in brain edemas The compound (I—Na) dissolved in physiological saline was put into an osmotic pressure pump buried in the back of a rat, and then administered through a polyethylene tube from the femoral vein from 10 minutes to 24 hours after the ischemia reperfusion (0.03–1.0 mg/kg/hour). As a result, the compound (I—Na) suppressed the formation of the brain edemas dose-dependently and significantly at a dose of 0.1–1.0 mg/kg/hour (FIG. 2). This effect was observed in all of the ACA area, the MCA area, and the caudate putamen. The effect is maximized at 0.3 mg/kg/hour and the minimum effective amount was considered to be 0.1 mg/kg/hour.

Experiment 3

Inhibitory effect of other endothelin antagonists on brain edemas

Figure 3:
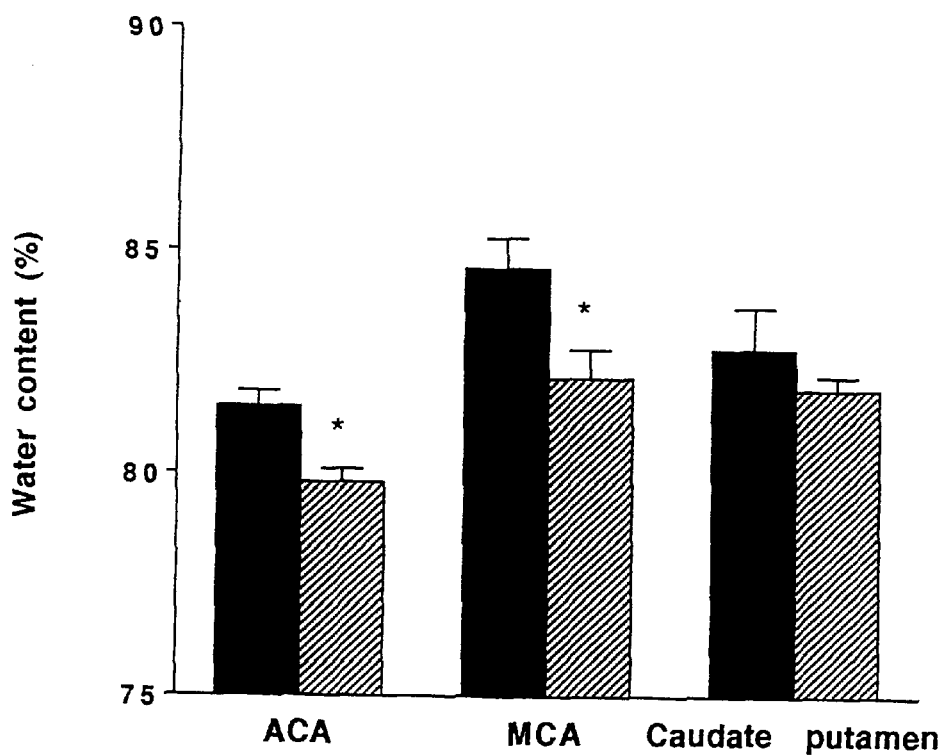
FIG. 3 shows an effect of bosentan on brain edemas. The ordinate represents the brain water content (%) and the abscissa represents the parts of brain. "ACA", "MCA" and "Caudate putamen" means the same as described above. The bars from the left, respectively represent a vehicle-administered group (N=5) and a post-ischemic-administered group (N=5). Data are represented by means of a standard error. The significant difference with P value <0.05 from a vehicle-administered group is represented by the asterisk.
Figure 4:
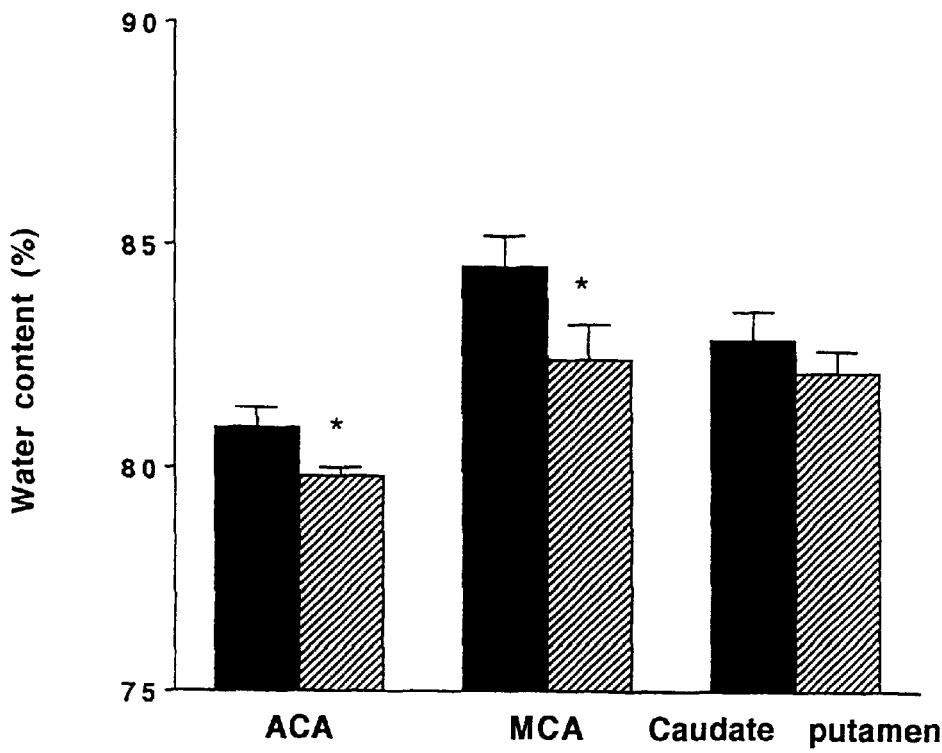
FIG. 4 shows an effect of TAK-044 on brain edemas. The ordinate represents the brain water content (%) and the abscissa represents the parts of brain. "ACA", "MCA" and "Caudate putamen" means the same as described above. The bars from the left, respectively represent a vehicle-administered group (N=7), a post-ischemic-administered group (N=7). Data are represented by means of a standard error. The significant difference with P value <0.05 from a vehicle-administered group is represented by the asterisk.
Figure 5:
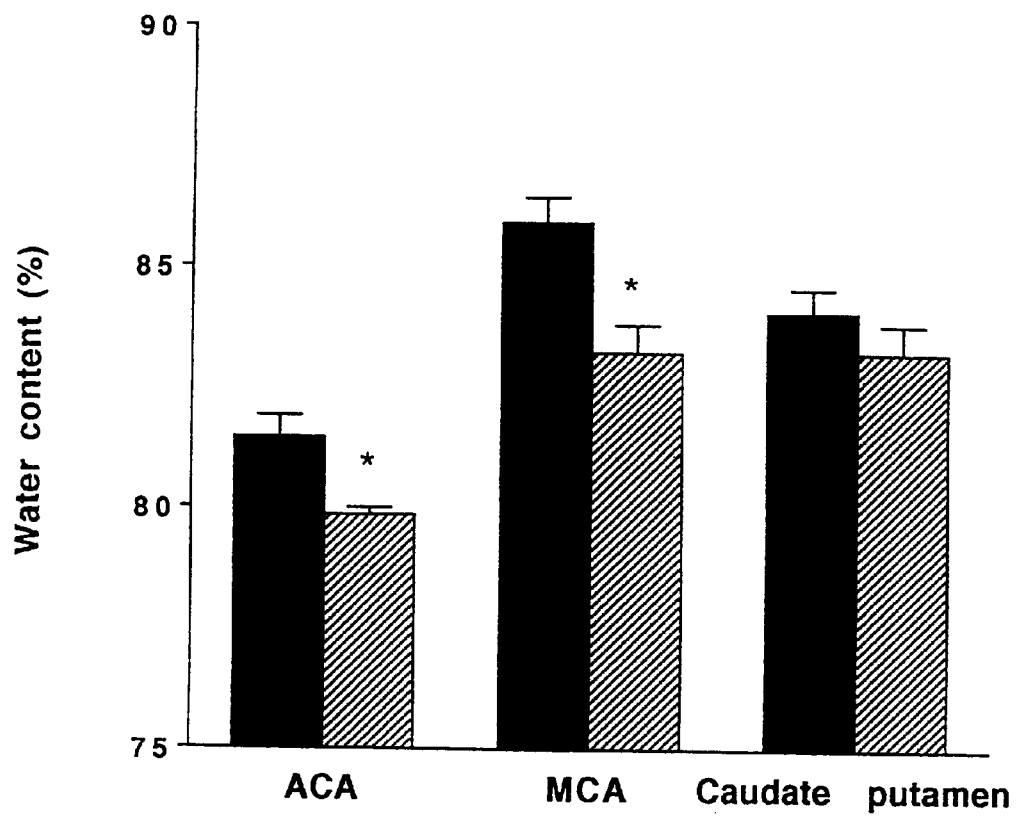
FIG. 5 shows an effect of BQ-123 on brain edemas. The ordinate represents the brain water content (%) and the abscissa represents the parts of brain. "ACA", "MCA" and "Caudate putamen" means the same as described above. The bars from the left, respectively represent a vehicle-administered group (N=8), a post-ischemic-administered group (N=7). Data are represented by means of a standard error. The significant difference with P value <0.05 from a vehicle-administered group is represented by the asterisk.

Each of Bosentan, TAK-044 and BQ-123 dissolved in physiological saline was put into an osmotic pump buried in the back of a rat and administered through a polyethylene tube from the crotch vein from 10 minutes to 24 hours after ischemia reperfusion (0.3/mg/kg/hour). As a result, the brain edema formation was significantly suppressed in the ACA and MCA areas and moderately in the caudate putamen (FIGS. 3, 4 and 5).

| Formulation 1 | |
|---|---|
| Compound (I–Na) | 50 mg |
| Lactose | 46 mg |
| Corn starch | 20 mg |
| Low-substituted hydroxypropylcellulose | 8 mg |
| Hydroxypropylmethylcellulose | 5 mg |
| Magnesium stearate | 1 mg |
| Total | 130 mg |

After all of the above ingredients except for hydroxypropylmethylcellulose and magnesium stearate was mixed uniformly, an 8% (w/w) aqueous solution of hydroxypropylmethylcellulose was added to the mixture as binders to give granules for tablet formation by a convenient wet granulation method. These granules were mixed with magnesium stearate and then formed into oral tablets (7 mm diameter and 130 mg per tablet) by a tablet press.

| Formulation 2 | |
|---|---|
| TAK-044 | 50 mg |
| Physiological saline | 200 ml |

TAK-044 was dissolved in physiological saline to give drip infusions.

EFFECT OF THE INVENTION

The composition for brain edemas of the present invention can be administered to treat or prevent brain edemas in such a situation that brain edemas have been or may be induced.

We claim:

1. A method for treating brain edemas in a patient, which comprises administering an effective amount of an endothelin antagonist having the formula

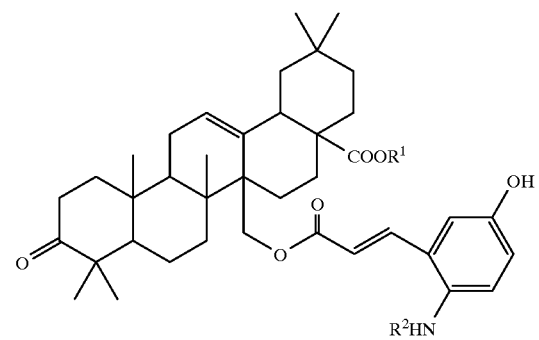

(I)

wherein $R^1$ is hydrogen and $R^2$ is —COCH=CHCOOH, or a pharmaceutically acceptable salts or hydrates thereof, to said patient.

* * * * *